(12) United States Patent
Axelsson et al.

(10) Patent No.: US 8,128,276 B2
(45) Date of Patent: Mar. 6, 2012

(54) DEVICE AT BONE CEMENT MIXER

(75) Inventors: Fredrik Axelsson, Malmö (SE); Ronny Bengtsson, Kristianstad (SE); Lars Wilander, Örkelljunga (SE)

(73) Assignee: Biomet Cementing Technologies AB, Sjobo (SE)

( * ) Notice: Subject to any disclaimer, the term of this patent is extended or adjusted under 35 U.S.C. 154(b) by 734 days.

(21) Appl. No.: 11/890,939

(22) Filed: Aug. 8, 2007

(65) Prior Publication Data
US 2008/0037365 A1 Feb. 14, 2008

(30) Foreign Application Priority Data
Aug. 11, 2006 (SE) ........................................ 0601667

(51) Int. Cl.
*B01F 13/00* (2006.01)
*B01F 11/00* (2006.01)
(52) U.S. Cl. ........................................ 366/130; 366/333
(58) Field of Classification Search .................. 366/130, 366/333
See application file for complete search history.

(56) References Cited

U.S. PATENT DOCUMENTS

| 5,015,101 A | 5/1991 | Draenert |
| 5,370,221 A | 12/1994 | Magnusson et al. |
| RE35,276 E * | 6/1996 | Chan .............................. 366/139 |
| 5,545,460 A | 8/1996 | Tanaka et al. |
| 5,549,380 A | 8/1996 | Lidgren et al. |
| 5,551,778 A | 9/1996 | Hauke et al. |
| 5,634,714 A * | 6/1997 | Guild .............................. 366/130 |
| 5,857,771 A | 1/1999 | Draenert |
| 6,312,149 B1 | 11/2001 | Sjovall et al. |
| 6,481,435 B2 * | 11/2002 | Hochrainer et al. ..... 128/200.14 |
| 6,635,044 B2 * | 10/2003 | Lopez .......................... 604/500 |
| 2004/0196735 A1 * | 10/2004 | Barker et al. ................. 366/139 |

FOREIGN PATENT DOCUMENTS

| EP | 1 466 572 A2 | 10/2004 |
| WO | WO 96/07472 A1 | 3/1996 |
| WO | WO 97/18031 A1 | 5/1997 |
| WO | WO 2005/096970 A2 | 10/2005 |

* cited by examiner

*Primary Examiner* — Walter D Griffin
*Assistant Examiner* — Christopher Vandeusen
(74) *Attorney, Agent, or Firm* — Tarolli, Sundheim, Covell & Tummino LLP

(57) ABSTRACT

A bone cement mixer (1) includes at least one mixing space (5) for mixing powder and liquid components (2, 4) to make bone cement. The powder component (2) is placed in the mixing space (5) and the liquid component (4) in a liquid container (3). The liquid component (4) is sucked out from the liquid container (3) to the mixing space (5) by means of a vacuum generated in the mixing space. The liquid container (3) is a tube (15) that has a connecting element (16) for connecting it to the bone cement mixer (1). The connecting element (16) is adapted to be opened when it is connected to a corresponding connecting element (17) on the bone cement mixer (1). The metal material of the tube has a thickness such that the volume of its liquid containing space (18) is brought to decrease when the vacuum in the mixing space (5) is brought to prevail therein.

24 Claims, 8 Drawing Sheets

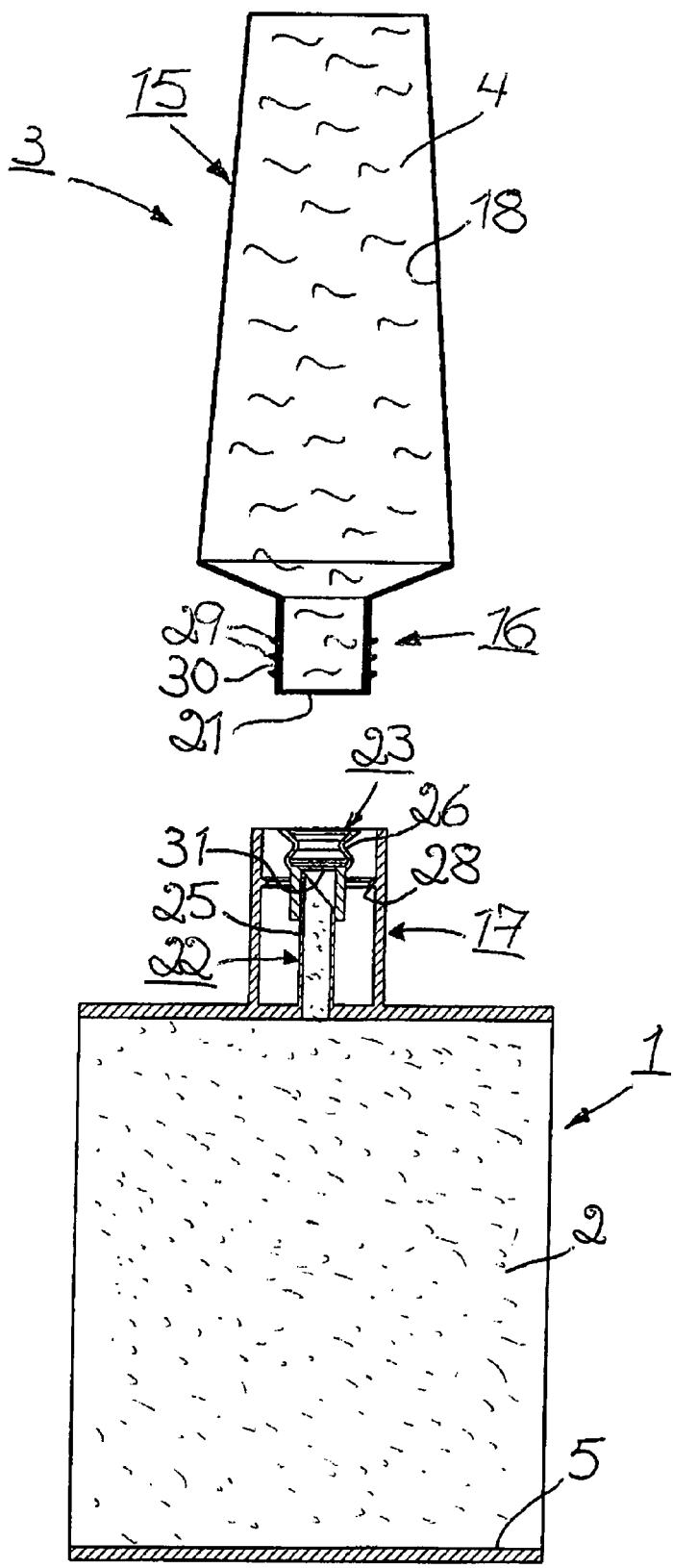

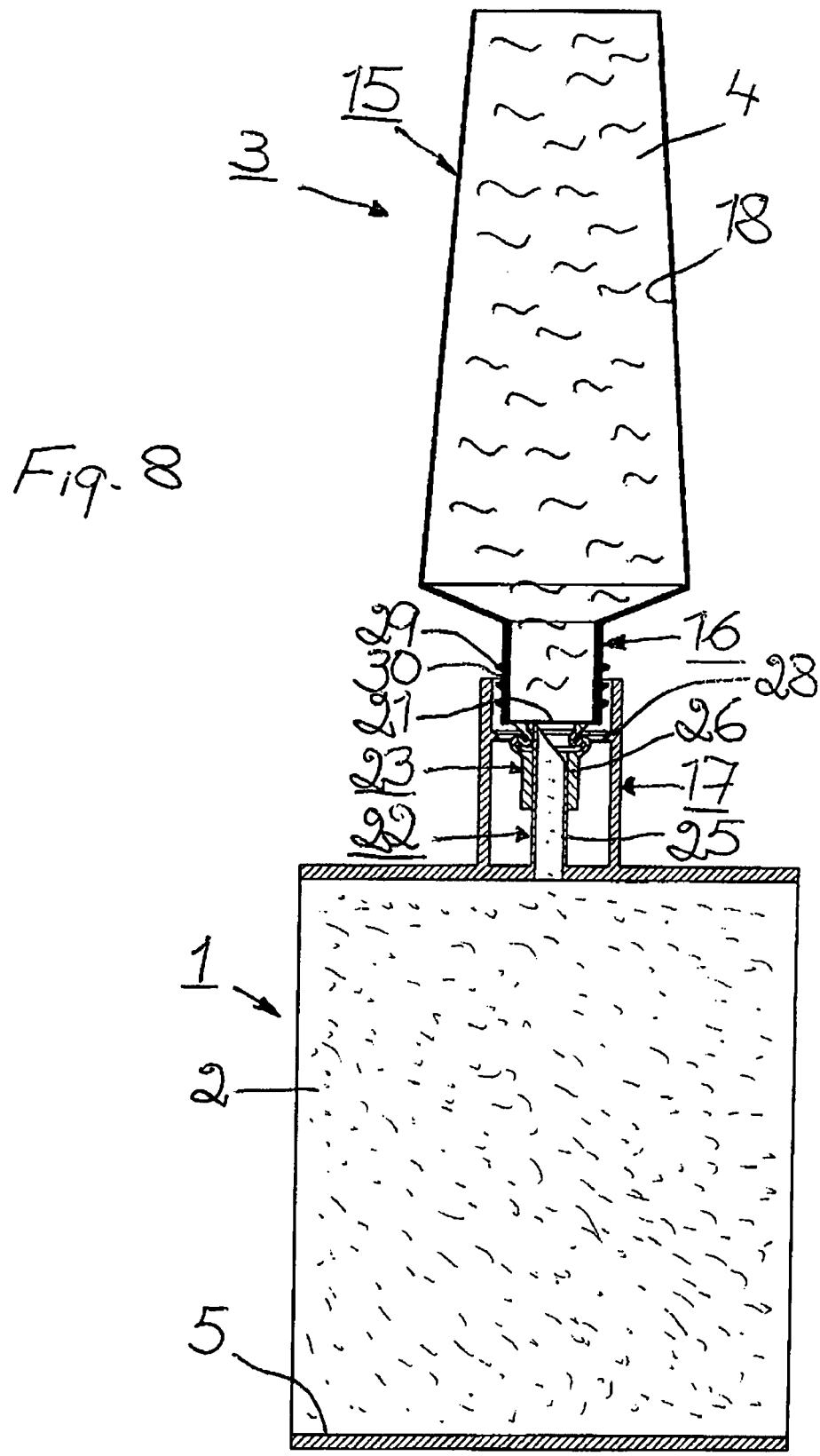

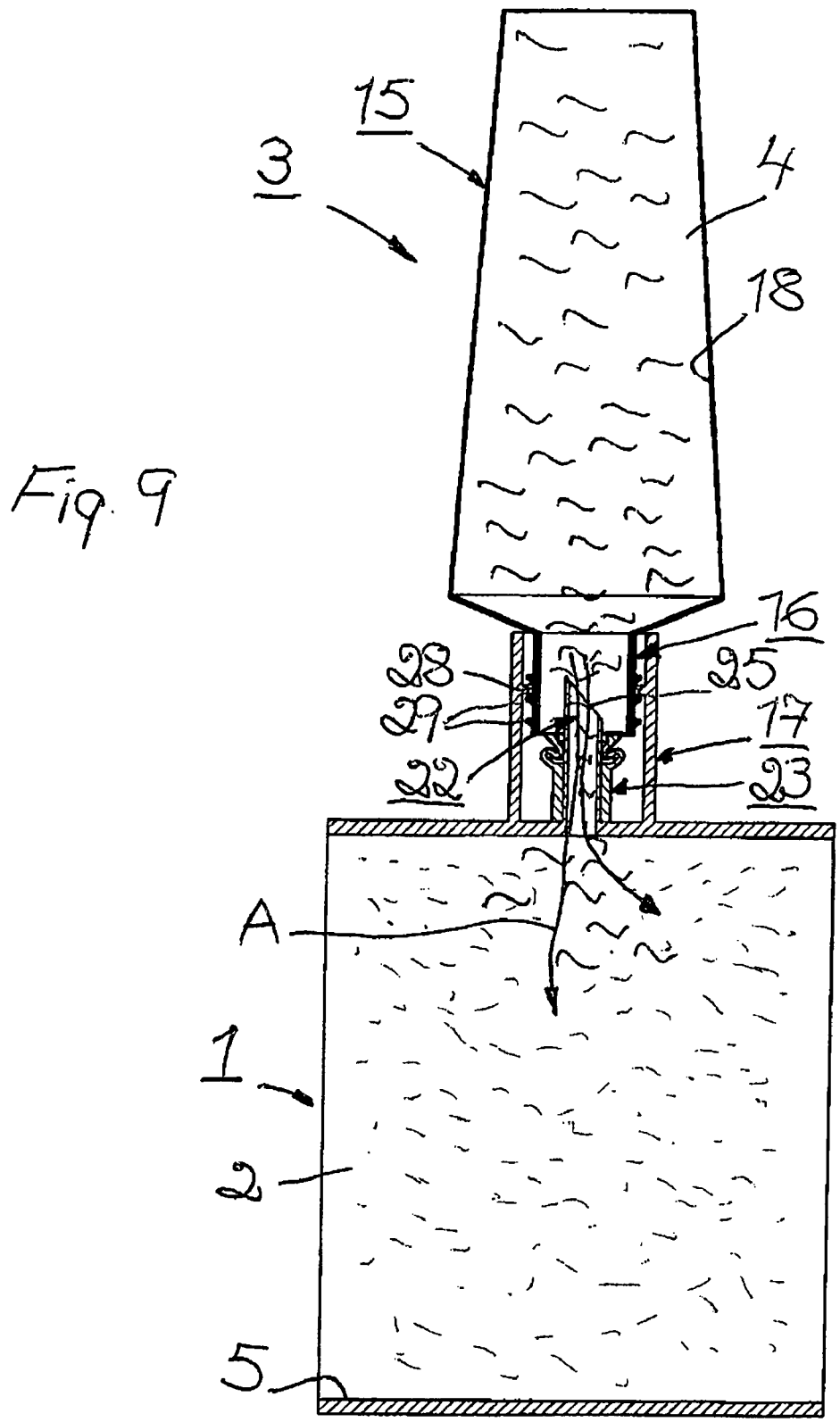

DEVICE AT BONE CEMENT MIXER

FIELD OF THE INVENTION

The present invention relates to a device at a bone cement mixer, wherein the bone cement mixer comprises at least one mixing space for mixing a powder component and a liquid component, preferably a polymer and a monomer respectively, to make bone cement, wherein the powder component is placed in the mixing space and the liquid component in a liquid container, and wherein the liquid component is sucked out from the liquid container to the mixing space and the powder component placed therein by means of vacuum generated in said mixing space.

BACKGROUND OF THE INVENTION

In U.S. Pat. No. 5,549,380, a bone cement mixer having a flexible liquid container for monomer, is described. Flexible monomer containers consist of a flexible wall material which provides for their flexibility, and a metal layer, preferably an aluminum layer, prevents the monomer from penetrating the flexible wall material. Thus, the walls of the monomer container consist of several layers, which means that the container is expensive to manufacture. Also, it is difficult to fill flexible monomer containers with monomer and to seal and open the container. Furthermore, flexible monomer containers are difficult to store, transport and handle and they are also sensible to blows and bumps.

SUMMARY OF THE INVENTION

It is an object of the invention to eliminate said drawbacks, which is achieved by means of the device mainly comprising the characterizing features indicated in claim 1 below.

Since the liquid container is a tube or bag with said characterizing features, a robust container is obtained which is easy and thereby inexpensive to manufacture and which is easy to fill, seal and open.

In U.S. Pat. No. 5,370,221 A there is described a vacuum container of metal which is provided inside another, flexible container for liquid and powder. The vacuum container is rigid. Thus, the vacuum container is not compressible and does not contain any liquid to be sucked out by means of a vacuum. Connecting elements as according to the invention are missing.

U.S. Pat. No. 5,551,778 A describes, inter alia, a liquid container of a metal foil. This liquid container is located inside a mixing container and is brought to burst by an overpressure applied thereto by a mixing means in the mixing container. Since the liquid container is found inside the mixing container, the liquid container has no connecting element for connection to the mixing container. Compression is not carried through by means of vacuum. The mixing container also lacks a corresponding connecting element for connection to the liquid container.

BRIEF DESCRIPTION OF THE DRAWINGS

The invention is described in more detail with reference to the attached drawings, in which:

FIGS. 7, 8 and 9 are sections through, inter alia, a third embodiment of a connecting element on the liquid container and through a corresponding connecting element on the bone cement mixer before, during and after their connection to one another;

DESCRIPTION OF EXAMPLE EMBODIMENTS

Figures 1, 10, 11:
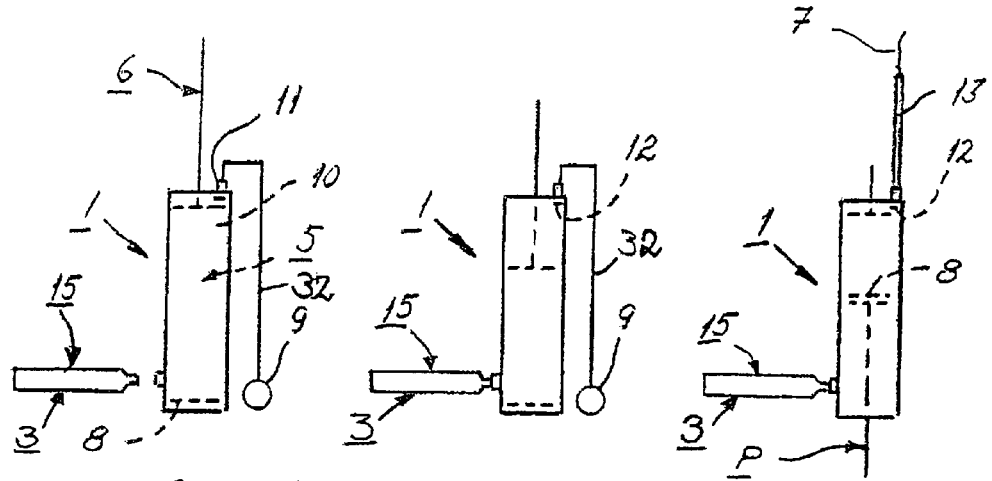
FIG. 1 depicts a liquid container in side view beside a bone cement mixer to which the container is to be connected.
FIG. 10 depicts the liquid container according to FIG. 1 in an empty state and connected to the bone cement mixer.
FIG. 11 depicts the bone cement mixer during delivery of bone cement from it.

The drawings depict a bone cement mixer 1 containing a powder component 2, preferably a polymer. It also depicts a liquid container 3 containing a liquid component 4, preferably a monomer.

The bone cement mixer 1 chosen by way of example is of a type similar to that referred to in U.S. Pat. No. 5,549,380. Thus, the bone cement mixer 1 has a mixing space 5 in which there is a powder component 2. Said bone cement mixer 1 also comprises a mixing means 6 which may be operable manually in order to mix the powder and liquid components 2, 4 situated in the mixing space 5 in order to make bone cement 7. The bone cement mixer 1 also comprises a delivery means 8 in the form of a piston which can in a known manner be anchored to the bone cement mixer in order to be held in position during the mixing of the powder and liquid components 2, 4. The delivery piston 8 can also in a known manner be released from the bone cement mixer 1 to allow it to be pressed by a delivery tool P into the mixing space 5 in order to deliver ready mixed bone cement 7 from the latter.

The bone cement mixer 1 is connectable to a vacuum source 9 adapted to generate vacuum in the mixing space 5 during mixing of the powder and liquid components 2, 4, and the vacuum is preferably maintainable during subsequent accumulation of ready mixed bone cement 7 in a delivery portion 10 of the mixing space 5. The vacuum source 9 is intended to generate such vacuum in the mixing space 5 that the porosity of the bone cement 7 is reduced or eliminated. For accumulation of bone cement 7, the vacuum source 9 is also adapted to suck the delivery piston 8 towards the delivery portion 10 in order to accumulate bone cement 7 in the latter. The delivery portion 10 has a nipple 11 or equivalent to which a hose 32 or equivalent from the vacuum source 9 is connectable in order to connect the bone cement mixer 1 to the vacuum source 9.

A filter 12 may be disposed in the delivery portion 10 within and/or around the nipple 11 in order to prevent powder or liquid components 2, 4 or bone cement 7 from being sucked out of the mixing space 5.

When bone cement 7 has been made in the bone cement mixer 1, the hose 32 from the vacuum source 9 is disconnected and a delivery pipe 13 is connected to the nipple 11. Thereafter, the delivery piston 8 with the feed tool P is pushed towards the delivery portion 10, thereby delivering the ready mixed bone cement 7 via the delivery pipe 13 (FIG. 11).

The liquid component 4 is in a liquid container 3 configured as a tube or bag, in the illustrated embodiments a tube 15, made of such metal material that its walls prevent the liquid component from escaping from it. The tube 15 has a connecting element 16 for connecting it to the bone cement mixer 1, and this connecting element 16 is adapted to be opened when it is connected to a corresponding connecting element 17 on the bone cement mixer 1. When the tube 15 is opened by being connected to the bone cement mixer 1, the liquid component 4 is sucked out of the aerosol container into the mixing space 5 (arrows A) by means of vacuum in the mixing space. The tube 15, or the bag, is designed and the metal material of the tube has such thickness that the volume of its liquid containing space 18 is brought to decrease when said vacuum in the mixing space 5 is brought to prevail also therein and the liquid component is sucked out therefrom.

The tube 15 has walls which are thick enough to render the tube rigidness when it contains the liquid component 4, but not thicker than the tube, as mentioned, can collapse due to pressure differentials between the inner and outer sides of the tube when the liquid component is sucked out therefrom, such that it is completely emptied of liquid component. The tube 15, or the bag, preferably consists of aluminum or an aluminum alloy.

In the embodiments depicted, the mixing space 5 in the bone cement mixer 1 is elongated, as is shown in FIGS. 1, 10 and 11, and the bone cement mixer's connecting element 17 is disposed radially relative to the longitudinal axis of the mixing space.

The connecting element 16 of the tube 15 and the corresponding connecting element 17 on the bone cement mixer 1 in the embodiments according to FIGS. 2 and 3 and FIGS. 4, 5 and 6 are designed to form together a threaded joint. For this purpose, the connecting element 16 of the tube 15 is preferably cylindrical and has threads, preferably outside threads 19, which make it possible for it to be screwed firmly to threads, preferably inside threads 20, on the corresponding preferably cylindrical connecting element 17 on the bone cement mixer 1. Alternatively, said connecting elements 16, 17 may together form a snap joint (FIGS. 7, 8 and 9), for which purpose the connecting element 17 of the bone cement mixer 1 may for example have a flange 28 pointing radially inwards which is fastenable by being snapped into a groove 30 delineated between flanges 29 pointing radially outwards on the corresponding connecting element 16 on the tube 15. According to another alternative embodiment (not depicted), said connecting elements 16, 17 may together form a bayonet joint. Other types of connection between the connecting elements 16, 17 are also possible.

The connecting element 16 of the tube 15, or bag, has a closing wall 21 which closes it. The closing wall 21 is openable by at least one opening means 22 on the bone cement mixer 1 when the connecting element 16 of the tube 15 is connected, in the embodiments depicted, by being screwed firmly or snapped on, to the bone cement mixer's connecting element 17. The opening means 22 is so configured or disposed as to allow the vacuum in the mixing space 5 to suck the liquid component 4 out from the space 18 in the tube 15 past (FIG. 3) or through (FIGS. 6 and 9) the opening means and into the mixing space. In the embodiments depicted, the opening means 22 is disposed in the connecting element 17 of the bone cement mixer 1 so that it pushes up at least one hole in the closing wall 21 of the tube 15 when the latter's connecting element 16 is connected, preferably by being screwed firmly or snapped on, to the connecting element 17 of the bone cement mixer. The opening means 22 is configured substantially as a needle 24 in FIGS. 2 and 3 and substantially as a cannula 25 in FIGS. 4 to 9, but may be of any suitable shape.

Figure 2:
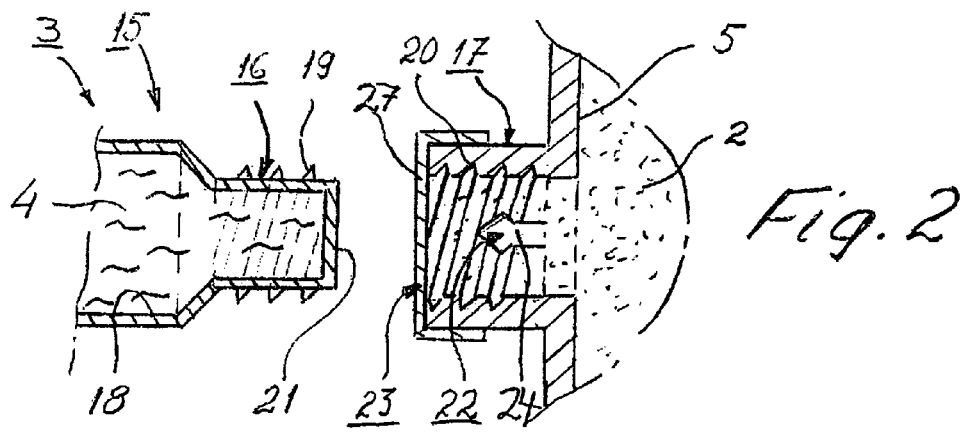
FIGS. 2 and 3 are sections through a first embodiment of a connecting element on the liquid container and through a corresponding connecting element on the bone cement mixer before and after their connection to one another.
Figure 3:
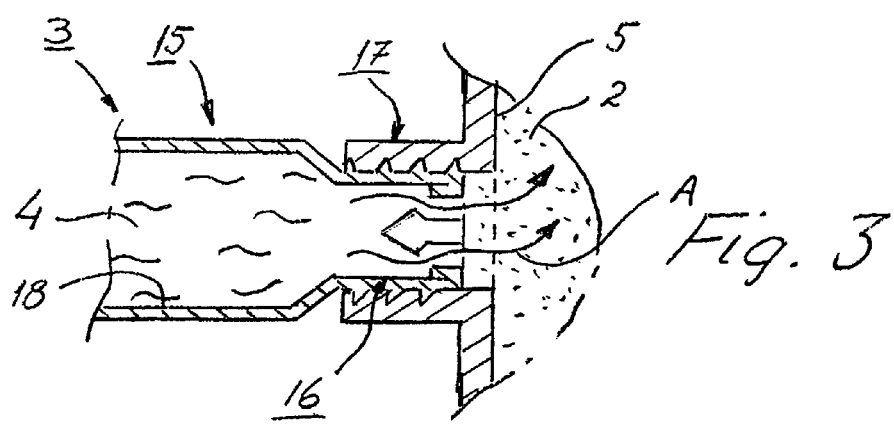
Figure 4:
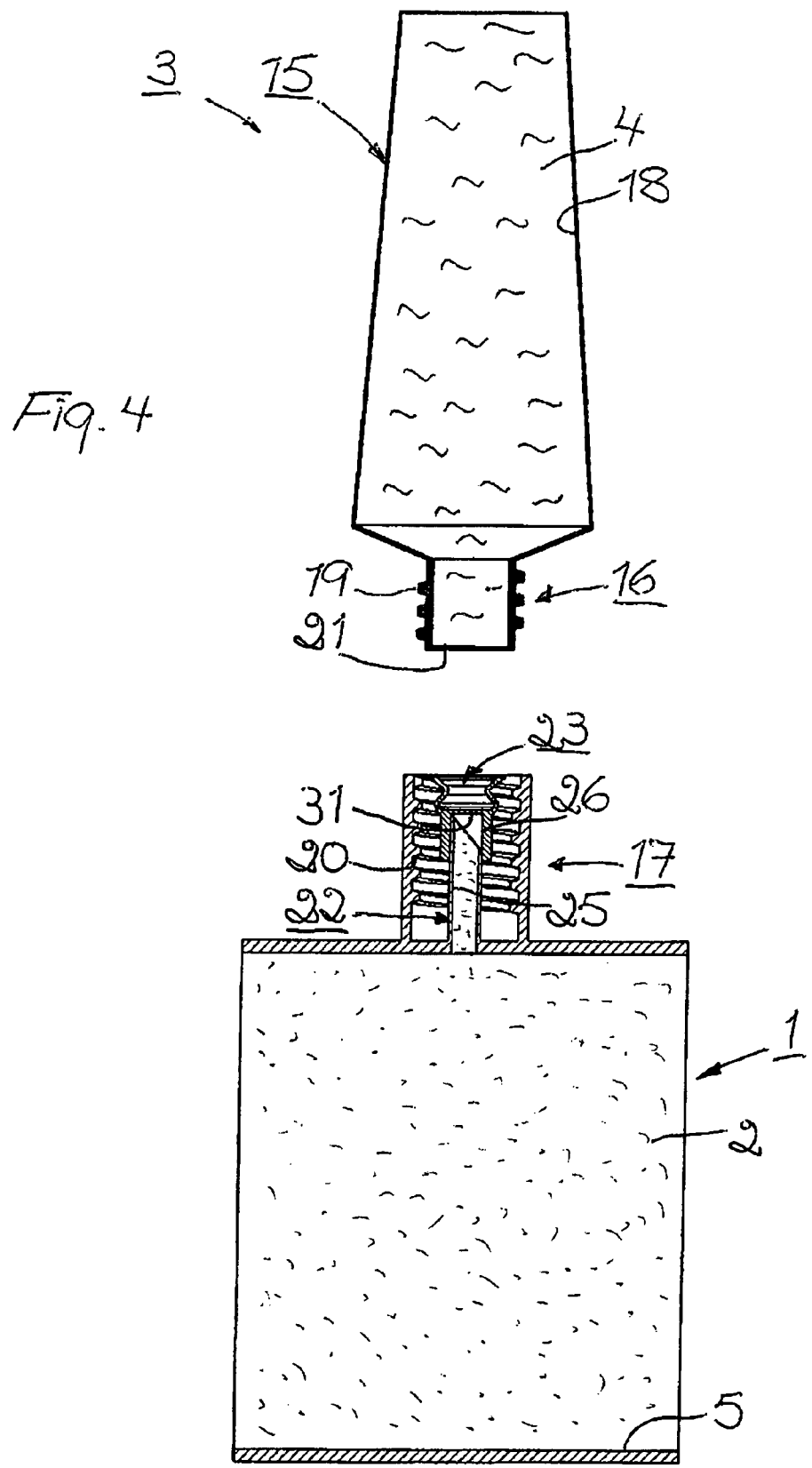
FIGS. 4, 5 and 6 are sections through, inter alia, a second embodiment of a connecting element on the liquid container and through a corresponding connecting element on the bone cement mixer before, during and after their connection to one another.
Figure 5:
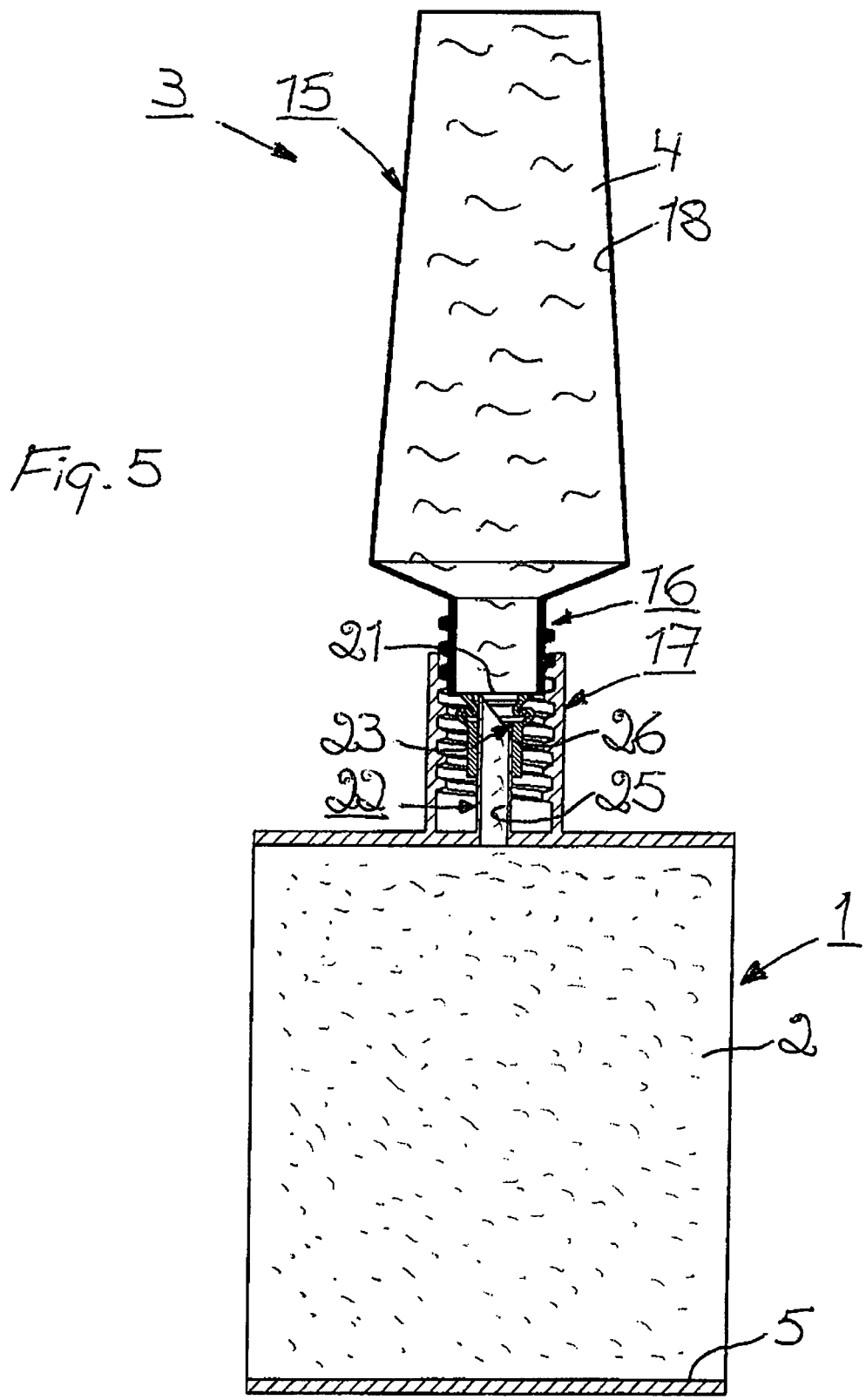
Figure 6:
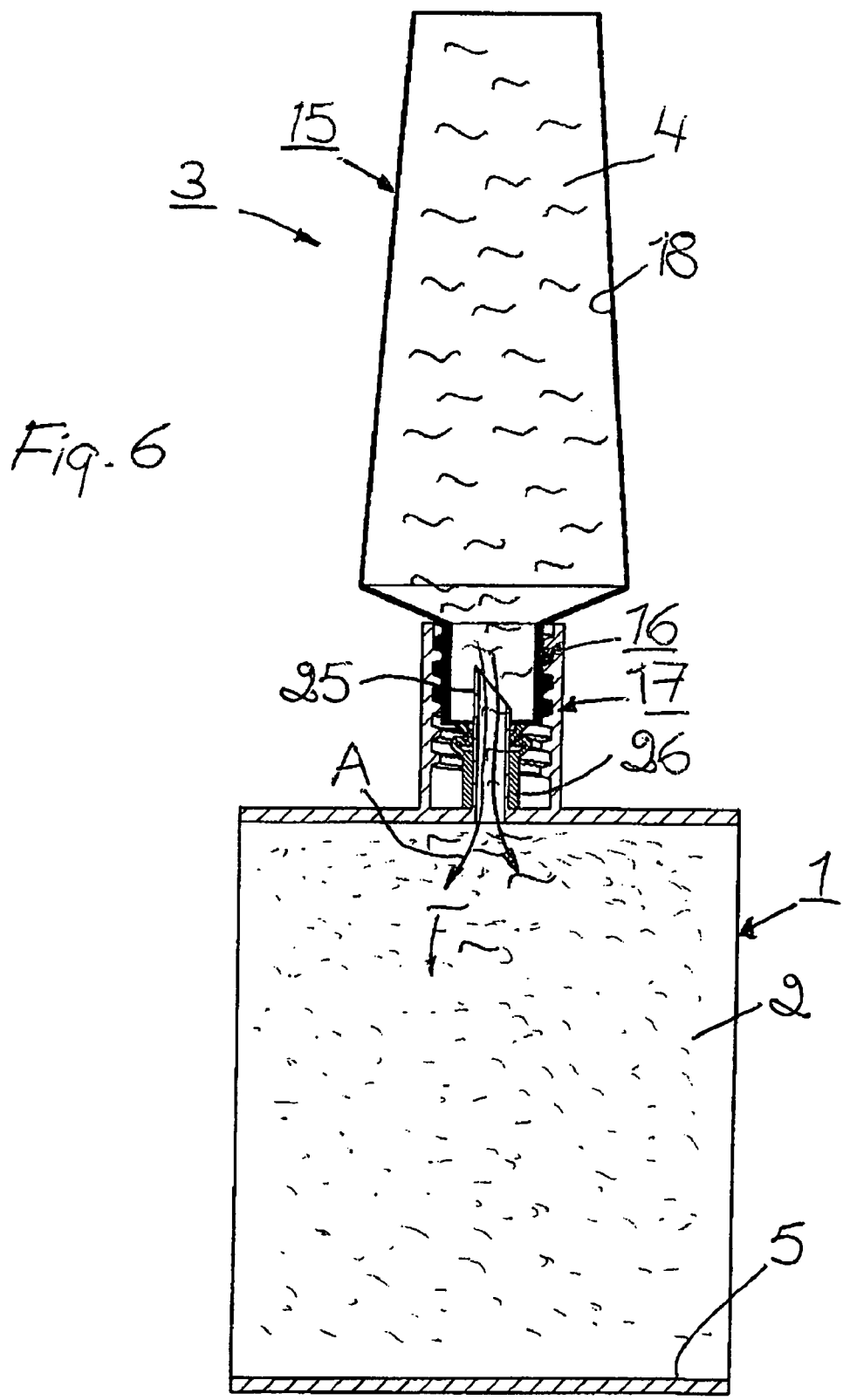

With a view to ensuring that the powder component 2 remains in the mixing space 5 of the bone cement mixer 1 and preventing its running out before the liquid component 4 is supplied as a result of cessation of vacuum therein, the connecting element 17 of the bone cement mixer has a seal 23 which closes this space. The seal 23 according to FIG. 2 is configured as a manually removable cap 27. The seal 23 according to FIGS. 4 to 9, in order to maintain the vacuum in the mixing space 5 of the bone cement mixer 1 until connection has been effected, is in this case openable by the opening means 22 when the connecting element 16 of the tube 15 is connected, in the embodiments depicted, by being screwed firmly or snapped on, to the connecting element 17 of the bone cement mixer 1. According to FIGS. 4 to 9, the opening means 22 takes the form, as indicated above, of a cannula 25 and the seal 23 takes the form of a rubber socket 26 placed over at least the tip of the cannula, whereby the cannula pushes up first a hole in a sealing wall 31 of the rubber socket and thereafter a hole in the closing wall 21 of the connecting element 16 of the tube 15 when the connecting element of the tube is connected, in the embodiments depicted, by being screwed firmly or snapped on, to the connecting element 17 of the bone cement mixer 1. Other types of seals 23 are also possible.

Figure 12:
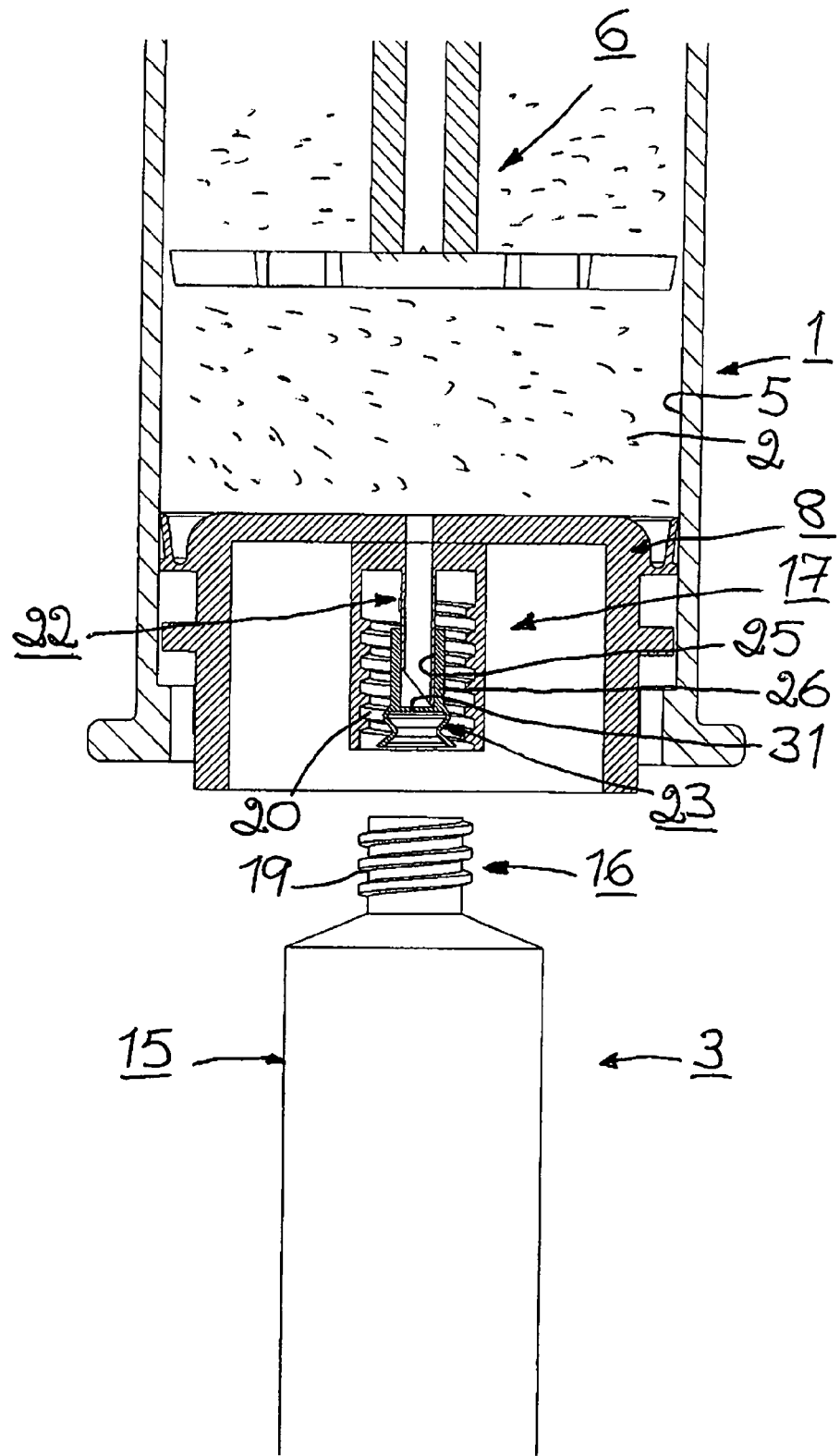
FIG. 12 depicts in section an alternative location of the connecting element on the bone cement mixer.

If the aerosol container 15 is intended to be used in association with a bone cement mixer 1 with a delivery piston 8, as in FIGS. 1, 10 and 11, it may alternatively be connected to the delivery piston, as illustrated by FIG. 12, which in that case is provided with a suitable type of connecting element 17 which fits to the connecting element 16 of the tube or bag, whereby the connecting elements 16, 17 together form a joint of a kind similar to that described above, e.g. a threaded joint with outside and inside threads 19 and 20 respectively, with suitable opening means 22 and a suitable seal 23.

As depicted in FIG. 12, the connecting element 17 on the delivery piston 8 is oriented in the latter's movement direction so that the connecting element 16 of the tube 15 or bag can be connected to it on the opposite side of the delivery piston from the mixing space 5.

The invention is not limited to the preferred embodiments described above and depicted in the drawings but may be varied within the scopes of the claims set out below. As examples of undepicted embodiments, it may be mentioned that the connecting elements 16, 17 may be configured and/or positioned in some other way, the opening means 22 may be configured and/or positioned in some other way and the bone cement mixer 1 may be configured in some other way. The powder and liquid components 2, 4 may possibly be components other than a polymer and a monomer respectively.

The invention claimed is:

1. A device comprising a bone cement mixer (1) and a liquid container (3), wherein:

the bone cement mixer (1) comprises at least one mixing space (5) for mixing of powder and liquid components (2, 4), preferably a polymer and a monomer respectively, to make bone cement, the powder component (2) is placed in the mixing space (5) and the liquid component (4) is placed in the liquid container (3), the liquid component (4) is sucked out from the liquid container (3) to the mixing space (5) and the powder component (2) placed therein by means of vacuum generated in said mixing space, the liquid container (3) is a tube (15) or bag of such metal material which prevents the liquid component (4) from escaping from it, the tube (15) or bag has a connecting element (16) with a closing wall (21) which closes the tube (15) or bag, the tube (15) or bag is adapted to being opened when it is connected to a corresponding connecting element (17) on the bone cement mixer (1), the connecting element (17) on the bone cement mixer (1) has a seal (23) which closes the mixing space (5) of the bone cement mixer (1), wherein the connecting element (17) has an opening means (22) which, when the connecting element (16) of the tube (15) or bag is connected to the connecting element (17) of the bone cement mixer (1), pushes up first a hole in the seal (23) and then in the closing wall (21) in the connecting element (16) of the tube (15) or bag, such that the vacuum in the mixing space (5) of the bone cement mixer (1) can suck the liquid component (4) out from a liquid containing space (18) in the tube (15) or bag, past or through the opening means (22), and into the mixing space (5), and wherein the tube (15) or bag is designed and the metal material of the tube or bag has a thickness such that the tube (15) or bag is rigid when it contains the liquid component (4) and such that the volume of its liquid containing space (18) is brought to decrease when said vacuum in the mixing space (5) is brought to prevail also therein when the liquid component is sucked out therefrom wherein the opening means push in the same direction through the seal (23) and the closing wall (21).

2. A device according to claim 1, wherein the tube or bag is an aerosol container (15) made of aluminum or an aluminum alloy.

3. A device according to claim 1, wherein the connecting element (16) of the tube (15) or bag and the corresponding connecting element (17) on the bone cement mixer (1) together form a threaded joint.

4. A device according to claim 3, wherein the connecting element (16) of the tube (15) or bag has threads (19), so that it can be screwed firmly to threads (20) on the connecting element (17) on the bone cement mixer (1).

5. A device according to claim 1, wherein the connecting element (16) of the tube (15) or bag and the corresponding connecting element (17) on the bone cement mixer (1) together form a snap joint.

6. A device according to claim 5, wherein the connecting element (17) of the bone cement mixer (1) has a flange (28) pointing radially inwards which can be snapped firmly into a groove (30) delineated between flanges (29) which point radially outwards on the corresponding connecting element (16) on the tube (15) or bag.

7. A device according to claim 1, wherein the connecting element (16) of the tube (15) or bag and the corresponding connecting element (17) on the bone cement mixer (1) together form a bayonet joint.

8. A device according to claim 1, wherein:
the opening means (22) is integrally formed with the bone cement mixer (1).

9. A device according to claim 1, wherein the opening means (22) takes the form of a cannula (25) and the seal (23) takes the form of a rubber socket (26) which is placed over the cannula, whereby the cannula pushes up first a hole in a sealing wall (31) of the rubber socket and thereafter a hole in the closing wall (21) of the connecting element (16) of the tube (15) or bag when the connecting element of the tube or bag is connected to the connecting element (17) of the bone cement mixer (1).

10. A device according to claim 1, wherein the tube (15) or bag is connectable to a bone cement mixer (1) which has at least one mixing means (6) for mixing the powder and liquid components (2, 4).

11. A device according to claim 1, wherein the tube (15) or bag is connectable to a bone cement mixer (1) which has means (11) for connection to a vacuum source (9) adapted to generate vacuum in the mixing space (5) of the bone cement mixer.

12. A device according to claim 11, wherein the vacuum source (9) is adapted to generate vacuum in the mixing space (5) during mixing of the powder and liquid components (2, 4) and to maintain this vacuum during accumulation of ready mixed bone cement in a delivery portion (10) of the mixing space (5), from which delivery portion (10) accumulated bone cement is to be delivered.

13. A device according to claim 11, wherein the tube (15) or bag is connectable to a bone cement mixer (1) which has at least one filter (12) for preventing the powder and liquid components (2, 4) and/or bone cement from being sucked out from the mixing space (5) by the vacuum source (9).

14. A device according to claim 1, wherein the tube (15) or bag is connectable to a bone cement mixer (1) which has a delivery means (8) in the form of a piston which is anchorable relative to the bone cement mixer and which can be released from the latter after the mixing of the powder and liquid components (2, 4), so that the delivery piston (8) can move and/or be moved relative to the mixing space (5) of the bone cement mixer.

15. A device according to claim 14, wherein the delivery piston (8) can be released from the bone cement mixer (1) and is adapted to delivering ready mixed bone cement from the mixing space (5).

16. A device according to claim 14, wherein the delivery piston (8) can be released and be sucked into the mixing space (5) by vacuum in the latter and is adapted to accumulate ready mixed bone cement in a delivery portion (10) of the mixing space (5).

17. A device according to claim 14, wherein the connecting element (17) of the bone cement mixer (1) is disposed on the delivery piston (8) for mechanically connecting the bone cement mixer (1) to the tube (15) or bag.

18. A device according to claim 17, wherein the connecting element (17) on the delivery piston (8) is oriented in the movement direction of the delivery piston (8) so that the connecting element (16) of the tube (15) or bag can be secured thereto on the opposite side of the delivery piston (8) from the mixing space.

19. A device according to claim 1, wherein the mixing space (5) is elongated and that the connecting element (17) of the bone cement mixer (1) is disposed radially relative to the longitudinal axis of the mixing space (5).

20. A device according to claim 4, wherein the connecting element (16) of the tube (15) or bag is cylindrical and has outside threads (19) so that it can be screwed firmly to inside threads (20) on the corresponding cylindrical connecting element (17) on the bone cement mixer (1).

21. A device according to claim 1, wherein the seal (23) closes the mixing space (5) and covers the opening means (22) to enclose the opening means (22) within the bone cement mixer (1).

22. A device according to claim 1, wherein, as the tube (15) or bag is being connected to the connecting element (17), the tube (15) or bag engages the seal (23) and pushes the seal (23) into engagement with the opening means (22) in order to open the seal (23) with the opening means (22) prior to the opening means (22) opening the tube (15) or bag.

23. A device according to claim 1, wherein the seal (23) and the tube (15) or bag is opened by the same portion of the opening means (22).

24. A device according to claim 1, wherein the opening means (22) extends away from the mixing space (5) for opening the seal (23) and the tube (15) or bag.

* * * * *